(12) United States Patent
Hasebe

(10) Patent No.: US 10,285,728 B2
(45) Date of Patent: May 14, 2019

(54) TROCAR AND METHOD FOR PRODUCING SAME

(71) Applicant: KAI R & D CENTER CO., LTD., Seki-shi, Gifu-ken (JP)

(72) Inventor: Kazuyuki Hasebe, Seki (JP)

(73) Assignee: KAI R&D CENTER CO., LTD., Seki-Shi, Gifu-Ken (JP)

( * ) Notice: Subject to any disclaimer, the term of this patent is extended or adjusted under 35 U.S.C. 154(b) by 351 days.

(21) Appl. No.: 15/106,874

(22) PCT Filed: Dec. 23, 2014

(86) PCT No.: PCT/JP2014/084010
§ 371 (c)(1),
(2) Date: Jun. 21, 2016

(87) PCT Pub. No.: WO2015/098898
PCT Pub. Date: Jul. 2, 2015

(65) Prior Publication Data
US 2016/0317176 A1  Nov. 3, 2016

(30) Foreign Application Priority Data
Dec. 26, 2013 (JP) .................................. 2013-269571

(51) Int. Cl.
*A61B 17/32* (2006.01)
*A61B 17/3209* (2006.01)
(Continued)

(52) U.S. Cl.
CPC ...... *A61B 17/3209* (2013.01); *A61B 17/3421* (2013.01); *A61F 9/007* (2013.01);
(Continued)

(58) Field of Classification Search
CPC ........ A61B 17/320016; A61B 17/3401; A61B 17/3472; A61B 17/3421; A61B 17/3454;
(Continued)

(56) References Cited

U.S. PATENT DOCUMENTS 3,308,822 A * 3/1967 De Luca ............. A61M 5/3286
604/274
3,460,255 A * 8/1969 Hutson ................ A61C 17/043
433/91
(Continued)

FOREIGN PATENT DOCUMENTS

| JP | 2011045604 A | 3/2011 |
|---|---|---|
| WO | 2006104060 A1 | 10/2006 |
| WO | 2011024816 A1 | 3/2011 |

OTHER PUBLICATIONS

International Search Report, PCT/JP2014/084010, dated Mar. 24, 2015, pp. 1-3.
(Continued)

*Primary Examiner* — Alexander J Orkin
(74) *Attorney, Agent, or Firm* — Cantor Colburn LLP

(57) ABSTRACT

A trocar has an insertion tube. A tube outlet of the insertion tube communicates with a collar of the insertion tube. An incision blade is provided to the tube outlet. The tube outlet opens toward the incision blade. The incision blade can thereby be inserted into an eyeball to form an incision, and the insertion tube can be inserted in the eyeball through the incision while the incision blade remains in the eyeball. Two lateral blade edges extend from a distal blade edge in the incision blade. The blade edges have outermost blade edges located in an outer region, which is a boundary surface, which includes the inner circumferential surface of the tube outlet. Therefore, the width dimension of the incision blade can be set greater than the inner diameter of the insertion tube.

10 Claims, 8 Drawing Sheets

(51) Int. Cl.
  *A61F 9/007* (2006.01)
  *A61B 17/34* (2006.01)
  *A61B 17/00* (2006.01)

(52) U.S. Cl.
  CPC ............... *A61B 2017/00526* (2013.01); *A61B 2017/3454* (2013.01)

(58) Field of Classification Search
  CPC . A61B 17/3209; A61B 17/34; A61B 17/3211; A61B 17/32093; A61F 2009/00887; A61F 9/00754
  See application file for complete search history.

(56) References Cited

U.S. PATENT DOCUMENTS

| | | | | |
|---|---|---|---|---|
| 4,258,716 A | * | 3/1981 | Sutherland | A61B 17/32001 606/170 |
| 4,368,738 A | * | 1/1983 | Tersteegen | A61B 17/3417 604/180 |
| 4,708,138 A | * | 11/1987 | Pazandak | A61F 9/00754 30/321 |
| 4,838,853 A | * | 6/1989 | Parisi | A61B 17/32001 601/2 |
| 5,820,609 A | * | 10/1998 | Saito | A61M 5/3286 604/272 |
| 2002/0038130 A1 | * | 3/2002 | Adams | A61B 17/32002 606/170 |
| 2008/0021399 A1 | * | 1/2008 | Spaide | A61B 17/3417 604/164.06 |
| 2010/0030105 A1 | | 2/2010 | Noishiki et al. | |
| 2012/0165851 A1 | | 6/2012 | Murakami et al. | |

OTHER PUBLICATIONS

International Preliminary Search Report on Patentability; International Application No. PCT/JP2014/084010; International Filing Date Dec. 23, 2014; dated Jun. 28, 2016, 7 pages.

* cited by examiner

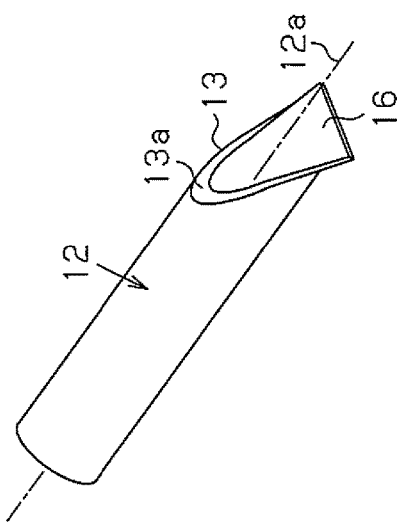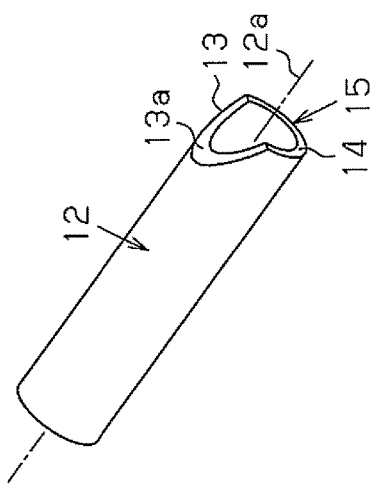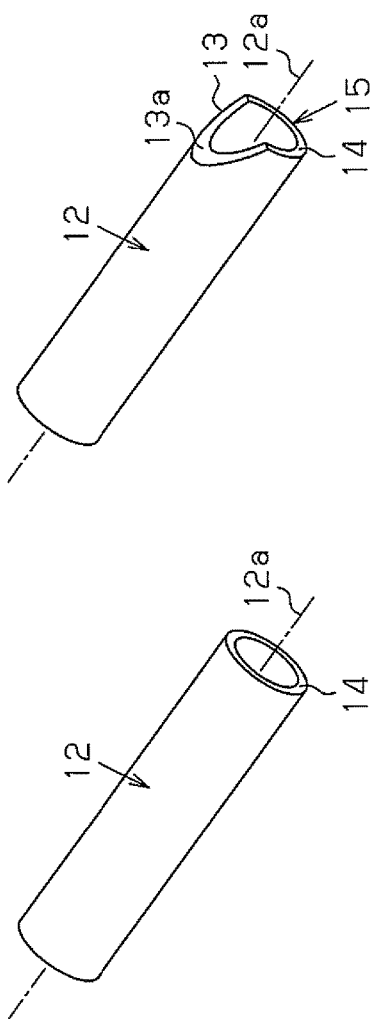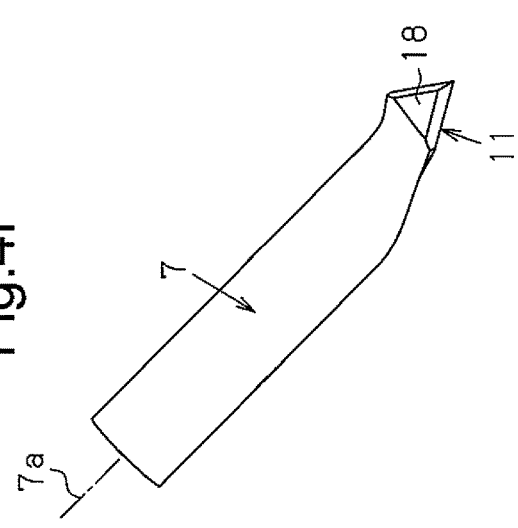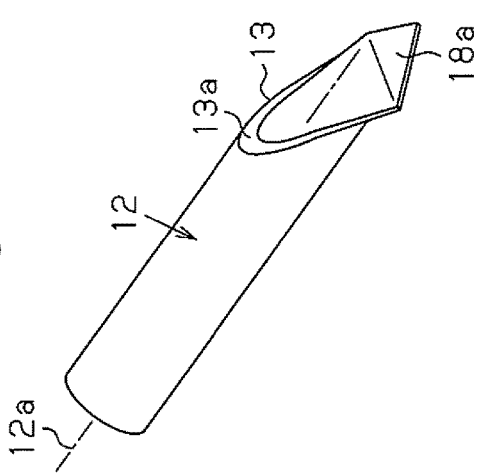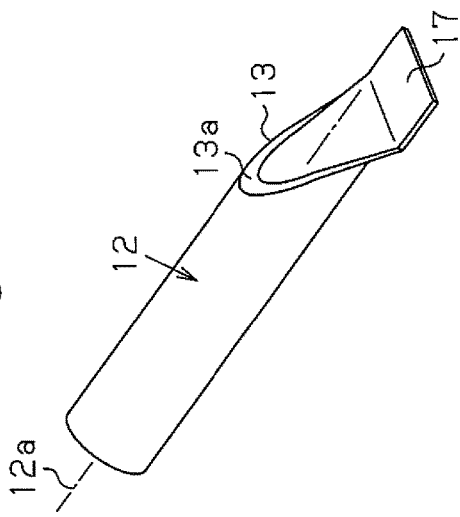

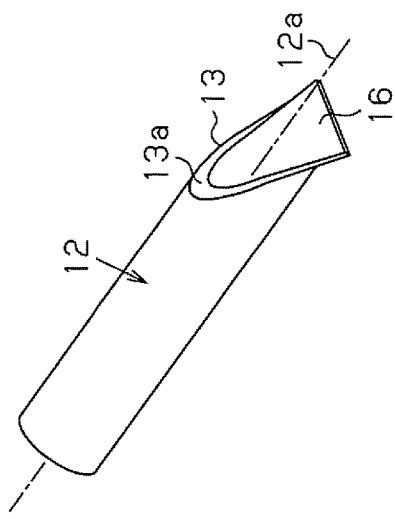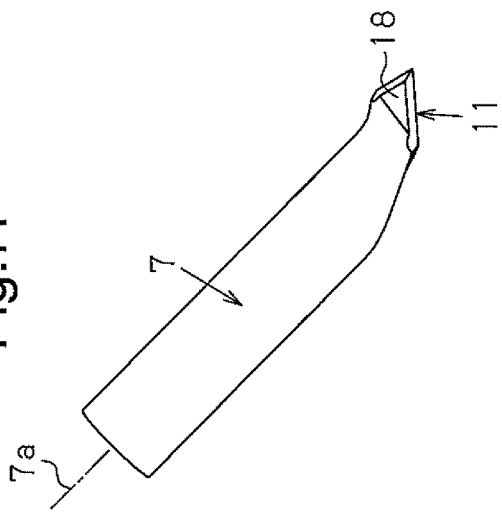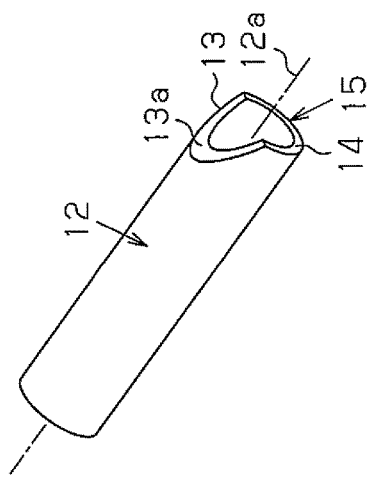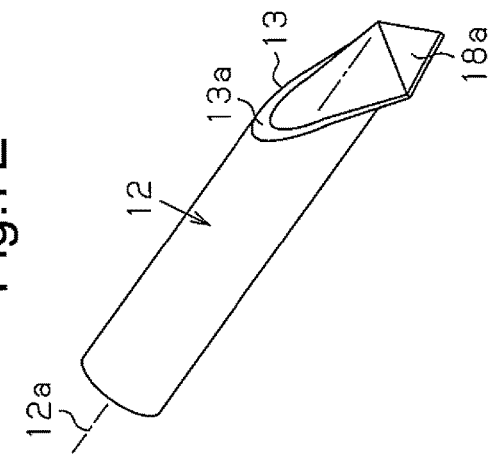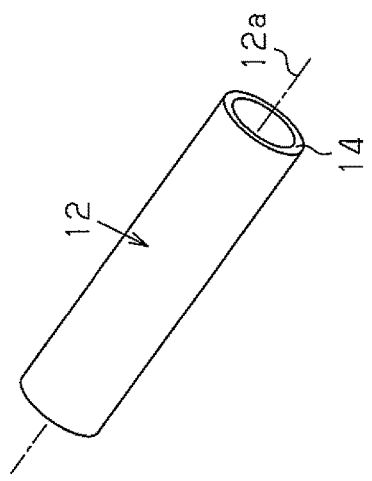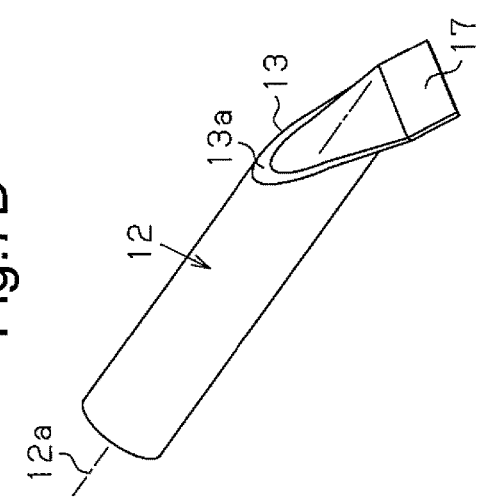

TROCAR AND METHOD FOR PRODUCING SAME

BACKGROUND OF THE INVENTION

The present invention relates to a trocar that is inserted and placed in an incision to guide a surgical instrument when the surgical instrument is inserted in an affected area such as an eyeball through the incision made in the affected area, thereby preventing excessive load from being applied to the incision. The present invention also relates to a method for manufacturing the trocar.

Conventionally, a two-step method has been employed as a method for inserting and placing a cannula (insertion tube) in an eyeball. In the two-step method, an incision tool and a trocar equipped with a cannula are separately prepared. An incision is formed in the eyeball with an incision blade of the incision tool in advance. The incision tool is then replaced with the trocar, and the trocar is inserted in the eyeball through the incision. The cannula is inserted and placed in the eyeball by withdrawing an inner needle of the trocar. Thus, there is no need to insert and withdraw the incision blade of the incision tool through the cannula. Furthermore, by setting the width dimension of the incision blade to be slightly greater than the outer diameter of the cannula, the incision dimension of the incision can be set to be slightly greater than the outer diameter of the cannula. Thus, when the trocar is inserted in the eyeball, excessive load is prevented from being applied to the incision, and the incision is allowed to heal easily.

For example, Patent Document 1 discloses a method for inserting and placing a cannula (insertion tube) using a trocar through a one-step method. In the one-step method, a trocar is prepared in which an incision tool is inserted in the cannula in advance from its proximal end toward its distal end such that the incision blade of the incision tool projects from the distal end of the cannula. To insert the trocar into the eyeball, first, an incision is formed by the incision blade, and subsequently, the cannula is inserted into the eyeball through the incision. The incision blade is then withdrawn from the cannula. In this manner, the cannula is inserted and placed in the eyeball. In the one-step method, since insertion of the incision blade and the cannula into the eyeball is performed in a single continuous operation, the insertion operation of the trocar is easy compared with the two-step method.

PRIOR ART DOCUMENT

Patent Document

Patent Document 1: Japanese Laid-Open Patent Publication No. 2011-45604

SUMMARY OF THE INVENTION

In the two-step method, the incision tool and the trocar need to be separately manipulated with respect to the eyeball, and the insertion and placing operation of the cannula is troublesome.

In the one-step method disclosed in Patent Document 1, since the incision blade of the incision tool needs to be inserted and withdrawn through the cannula, the width dimension of the incision blade must be set to be less than or equal to the inner diameter of the cannula. Thus, the incision dimension of the incision is reduced compared with the two-step method. In this case, when the trocar is inserted into the eyeball, the insertion resistance may be increased or the incision may be expanded, applying force in a direction to tear the opposite ends of the incision. This results in excessive load on the incision, and the incision may be hard to heal.

The conventional two-step method and one-step method have contradictory advantages and disadvantages in the operability and the incision dimension as described above.

Accordingly, it is a first objective of the present invention to facilitate insertion and placement of a trocar like the advantage in the operability according to the one-step method, and it is a second objective of the present invention to prevent excessive load from being applied to the incision during insertion and placement of the insertion tube like the advantage in the incision dimension according to the two-step method.

To achieve the foregoing objective and in accordance with a first aspect of the present invention, a trocar including an insertion tube is provided. The insertion tube includes a tube inlet located at a proximal end of the insertion tube and a tube outlet that communicates with the tube inlet and is located at a distal end of the insertion tube. The insertion tube includes an incision blade at the distal end. The tube outlet opens toward the incision blade. The incision blade includes a distal blade edge, which starts to incise an affected area when the distal blade edge is inserted in the affected area, and an outer blade edge that extends from the distal blade edge toward the tube outlet of the insertion tube. The insertion tube is divided into an inner region, which is inside a boundary surface along an inner circumferential surface of the tube outlet, and an outer region, which is outside the boundary surface. The outer blade edge includes an outermost blade edge located in the outer region.

With this configuration, since the outermost blade edge of the incision blade is located in the outer region at the tube outlet of the insertion tube, the width dimension of the incision blade can be set to be greater than the width dimension of the inner circumferential surface of the insertion tube. Thus, the incision dimension of the incision is increased, and when the insertion tube is inserted and placed in the affected area through the incision, load applied to the incision by the insertion tube is reduced. This allows the incision to heal easily.

To achieve the foregoing objective and in accordance with a second aspect of the present invention, a trocar including an insertion tube is provided. The insertion tube includes a tube inlet located at a proximal end of the insertion tube and a tube outlet that communicates with the tube inlet and is located at a distal end of the insertion tube. The insertion tube includes an incision blade at the distal end. The tube outlet opens toward the incision blade. The incision blade includes a distal blade edge, which starts to incise an affected area when the distal blade edge is inserted in the affected area, and an outer blade edge that extends from the distal blade edge toward the tube outlet of the insertion tube. The outer blade edge includes an outermost blade edge. The distance between a center line of the insertion tube and the outermost blade edge is set to be greater than the distance between the center line of the insertion tube and the inner circumferential surface of the tube outlet.

With this configuration, since the distance between the outermost blade edge of the incision blade and the center line of the insertion tube is set to be greater than the distance between the center line and the inner circumferential surface of the tube outlet, the width dimension of the incision blade can be set to be greater than the width dimension of the inner circumferential surface of the insertion tube. Thus, the incision dimension of the incision is also increased, and when the insertion tube is inserted and placed in the affected area through the incision, load applied to the incision by the insertion tube is reduced. This allows the incision to heal easily.

In a width direction orthogonal to the center line of the insertion tube, the distance between the center line of the insertion tube and the outermost blade edge is preferably set to be greater than the distance between the center line of the insertion tube and an outer circumferential surface of the tube outlet.

With this configuration, the width dimension of the incision blade can be set to be greater than the width dimension of the outer circumferential surface of the insertion tube, and the incision dimension of the incision is further increased. Thus, when the insertion tube is inserted and placed in the affected area through the incision, load applied to the incision by the insertion tube is further reduced, and the incision is allowed to heal easily.

To achieve the foregoing objective and in accordance with a third aspect of the present invention, a trocar including an insertion tube is provided. The insertion tube includes a tube inlet located at a proximal end of the insertion tube and a tube outlet that communicates with the tube inlet and is located at a distal end of the insertion tube. The insertion tube includes an incision blade at the distal end. The tube outlet opens toward the incision blade. The incision blade includes a distal blade edge, which starts to incise an affected area when the distal blade edge is inserted in the affected area, and an outer blade edge that extends from the distal blade edge toward the tube outlet of the insertion tube. The incision blade is configured such that the incision blade is inserted in the affected area to form an incision in the affected area, and the insertion tube is allowed to be inserted and placed in the affected area through the incision with the incision blade remaining in the affected area.

With this configuration, the incision blade is inserted in the affected area to form an incision, and with the incision blade remaining in the affected area, the insertion tube can be inserted and placed in the affected area through the incision.

The distal blade edge of the incision blade is preferably located in the outer region.

With this configuration, at the tube outlet of the insertion tube, the distal blade edge of the incision blade is located in the outer region. Thus, although the incision blade is kept at the tube outlet of the insertion tube, the distal blade edge is not located inside the inner circumferential surface of the insertion tube. Thus, when the surgical instrument is inserted in the tube inlet of the insertion tube to project from the tube outlet, the incision blade does not come in the way of the surgical instrument.

The distal blade edge of the incision blade is preferably located in the inner region.

With this configuration, if the width dimension of the surgical instrument is small compared with the width dimension of the inner circumferential surface of the insertion tube, the surgical instrument can be smoothly inserted and removed through the insertion tube with the incision blade kept at the tube outlet of the insertion tube.

The outer blade edge of the incision blade is preferably one of a plurality of outer blade edges located on an outer circumference of the center line of the insertion tube. With this configuration, the multiple outer blade edges facilitate forming an incision in the affected area.

The incision blade preferably has an inclined surface that is located between the tube outlet and the outer blade edge and that is inclined with respect to the center line of the insertion tube. With this configuration, the insertion tube is guided through the incision by the inclined surface and is easily inserted and placed in the affected area.

The inclined surface preferably extends such that the space inside the inclined surface in the width direction of the insertion tube orthogonal to a longitudinal direction of the insertion tube, which connects the tube inlet and the tube outlet, gradually increases toward the outer blade edge of the incision blade. With this configuration, the outer blade edge of the incision blade smoothly extends from the inclined surface.

The incision blade is preferably formed integrally with the tube outlet. With this configuration, the incision blade is easily provided at the tube outlet.

In the incision blade, the blade portion, which includes the distal blade edge and the outer blade edge, is preferably plate-shaped. In this case, since the incision blade is plate-shaped, the blade portion forms a linear incision in the affected area. The incision blade is easily provided at the tube outlet.

The incision blade is preferably configured such that the incision blade is inserted in the affected area to form an incision in the affected area, and the insertion tube is preferably allowed to be inserted and placed in the affected area through the incision with the incision blade remaining in the affected area. With this configuration, as mentioned above, when the insertion tube is inserted and placed in the affected area through the incision, load applied to the incision by the insertion tube is reduced, and the incision is allowed to heal easily.

The outer blade edge of the incision blade is preferably one of a plurality of outer blade edges located on an outer circumference of a center line of the insertion tube. The distal blade edge of the incision blade is preferably located at a position where the outer blade edges of the incision blade intersect each other in the outer region. With this configuration, the distal blade edge of the incision blade is located in the outer region at the tube outlet of the insertion tube. Thus, although the incision blade is kept at the tube outlet of the insertion tube, the distal blade edge is not located inside the inner circumferential surface of the insertion tube. Since the incision blade does not come in the way when the surgical instrument is inserted in the insertion tube, the surgical instrument is allowed to project from the tube outlet of the insertion tube. Furthermore, since the distal blade edge is pointed, an incision is easily made in the affected area.

The outer blade edge of the incision blade is preferably one of a plurality of outer blade edges located on an outer circumference of a center line of the insertion tube. The distal blade edge of the incision blade is preferably located at a position where the outer blade edges of the incision blade intersect each other in the inner region. With this configuration, if the width dimension of the surgical instrument is small compared with the width dimension of the inner circumferential surface of the insertion tube, the surgical instrument can be smoothly inserted and removed through the insertion tube with the incision blade kept at the tube outlet of the insertion tube. Furthermore, since the distal blade edge is pointed, the incision is easily made in the affected area.

The outer blade edges of the incision blade are desirably separate from the center line of the insertion tube in the width direction of the insertion tube orthogonal to the longitudinal direction of the insertion tube, which connects the tube inlet and the tube outlet. With this configuration, although the incision blade is kept at the tube outlet of the insertion tube, the distal blade edge is separate from the inner circumferential surface of the insertion tube. Thus, when the surgical instrument is inserted in the insertion tube, the incision blade does not come in the way, and the surgical instrument is allowed to project from the tube inlet of the insertion tube.

The outer blade edges of the incision blade are preferably a pair of outer blade edges located around the center line of the insertion tube. With this configuration, an incision is easily formed in the affected area using the pair of outer blade edges.

The space between the outer blade edges of the incision blade preferably gradually increases from the distal blade edge of the incision blade toward the tube outlet of the insertion tube. With this configuration, an incision is easily formed in the affected area by arranging the outer blade edges of the incision blade in, for example, V-shape.

The outer blade edge of the incision blade is preferably continuous with the inclined surface. With this configuration, the insertion tube is guided through the incision by the inclined surface and is easily inserted and placed in the affected area.

The inclined surface of the incision blade preferably extends continuously from the tube outlet. This configuration smoothly guides through the incision with the inclined surface.

In the incision blade, the blade portion, which includes the distal blade edge and the outer blade edge, preferably extends along the center line of the insertion tube. With this configuration, the blade portion is easily inserted in the affected area, and the insertion tube is easily inserted and placed in the incision formed by the outer blade edge of the incision blade.

In the incision blade, the blade portion, which includes the distal blade edge and the outer blade edge, preferably extends along the inclined surface of the incision blade. With this configuration, the insertion tube is easily inserted and placed in the incision formed by the outer blade edge of the incision blade. The blade portion is further separate from the inner circumferential surface of the insertion tube although the incision blade is kept at the tube outlet of the insertion tube. Thus, the incision blade does not come in the way of the surgical instrument.

A holder is preferably detachably coupled to the tube inlet of the insertion tube. With this configuration, the convenience of the trocar is improved by attaching or detaching the holder to the tube inlet of the insertion tube.

To achieve the foregoing objective and in accordance with a fourth aspect of the present invention, a method for manufacturing a trocar is provided that includes: forming a cutout area by cutting an end of a tubular member such that the cutout area is inclined with respect to a center line of the tubular member, and forming a cut portion by leaving part of an end face of the tubular member to be continuous with the cutout area; forming a projecting portion by pressing the cut portion; forming a blade plate portion by trimming the projecting portion; and forming a blade portion by sharpening the blade plate portion. With this configuration, the incision blade is easily formed integrally with the end portion of the tubular member.

BRIEF DESCRIPTION OF THE DRAWINGS

FIGS. 4A to 4F are perspective views of processes for manufacturing the trocar according to the first embodiment.

FIGS. 7A to 7F are perspective views of processes for manufacturing the trocar according to the second embodiment.

DETAILED DESCRIPTION OF THE PREFERRED EMBODIMENTS

A first embodiment of the present invention will now be described with reference to FIGS. 1 to 4 and 8A.

Figure 1A:
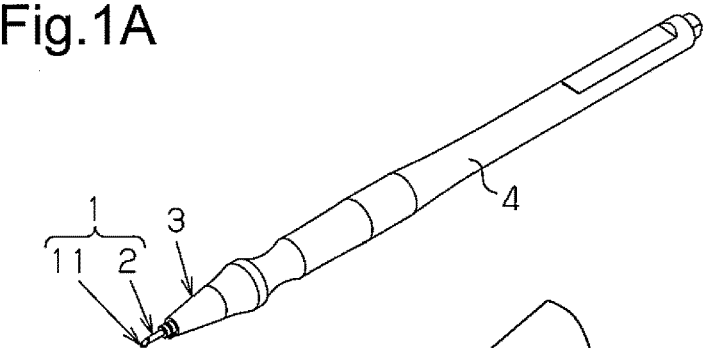
FIG. 1A is a perspective view illustrating an assembled state of a trocar according to a first embodiment, in which the trocar is coupled to a holder.
Figure 8A:
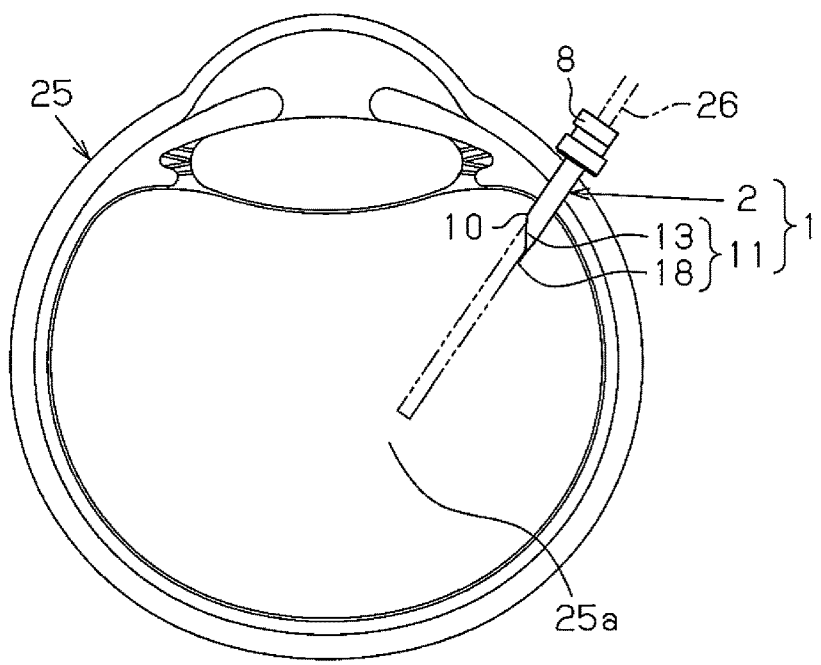
FIG. 8A is a schematic diagram illustrating the trocar according to the first embodiment in use.
Figure 8B:
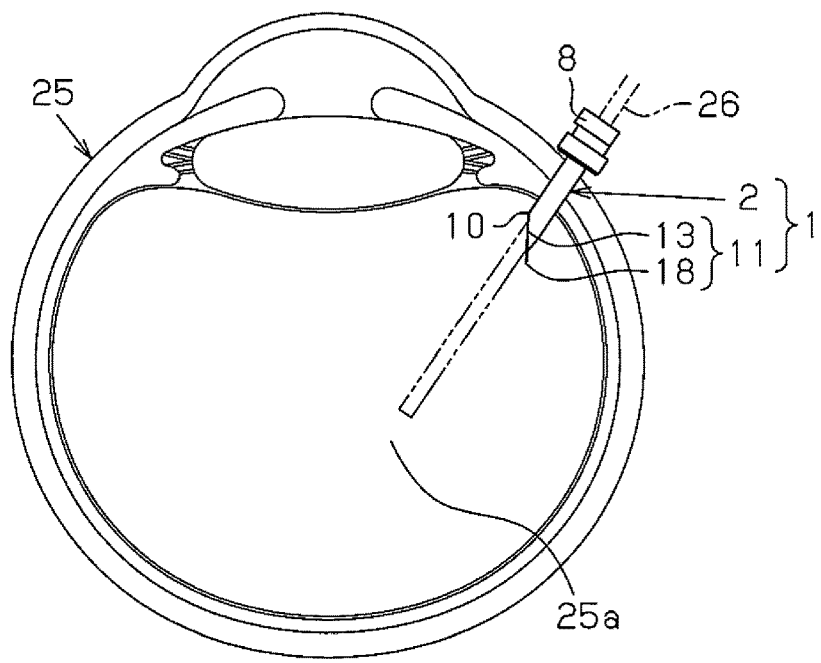
FIG. 8B is a schematic diagram illustrating the trocar according to the second embodiment in use.

As shown in FIG. 1A, a trocar 1 includes, for example, an insertion tube 2, which can be inserted and placed in an affected area such as an eyeball 25 as shown in FIG. 8A, and an incision blade 11, which forms an incision in the eyeball 25. A holder 3 is detachably coupled to the insertion tube 2.

Figure 1B:
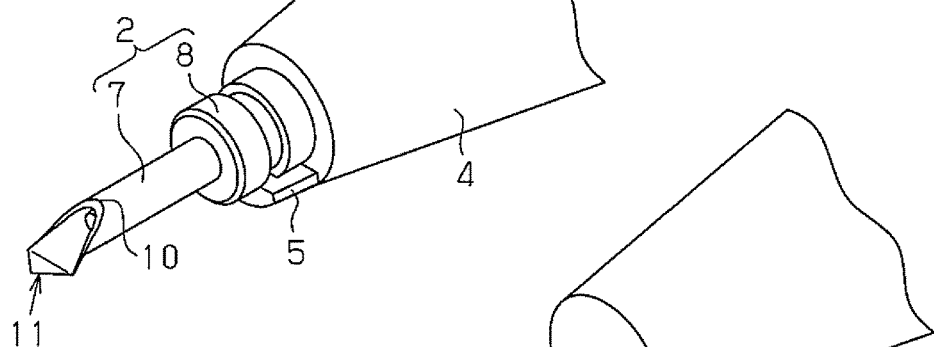
FIG. 1B is a partially enlarged perspective view of the trocar of FIG. 1A.
Figure 1C:
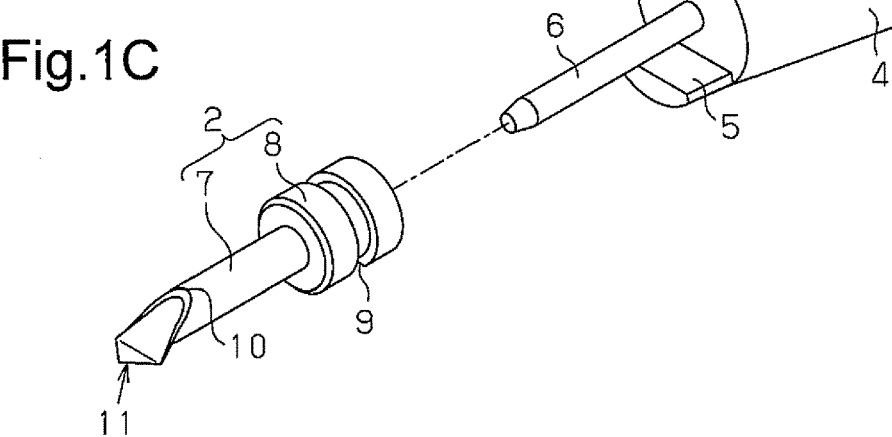
FIG. 1C is an exploded partial perspective view of the trocar of FIG. 1B.
Figure 1D:
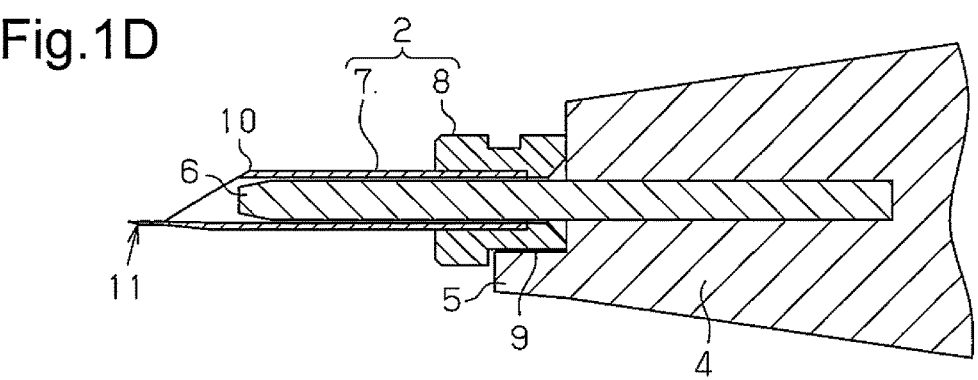
FIG. 1D is a cross-sectional view of the trocar of FIG. 1B.
Figure 2A:
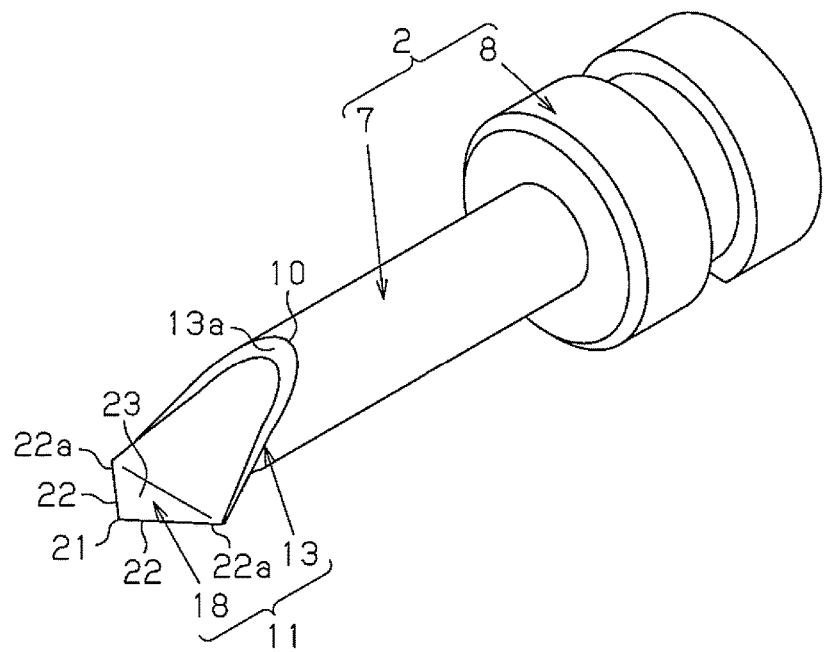
FIG. 2A is an enlarged perspective view of the trocar according to the first embodiment.
Figure 2B:
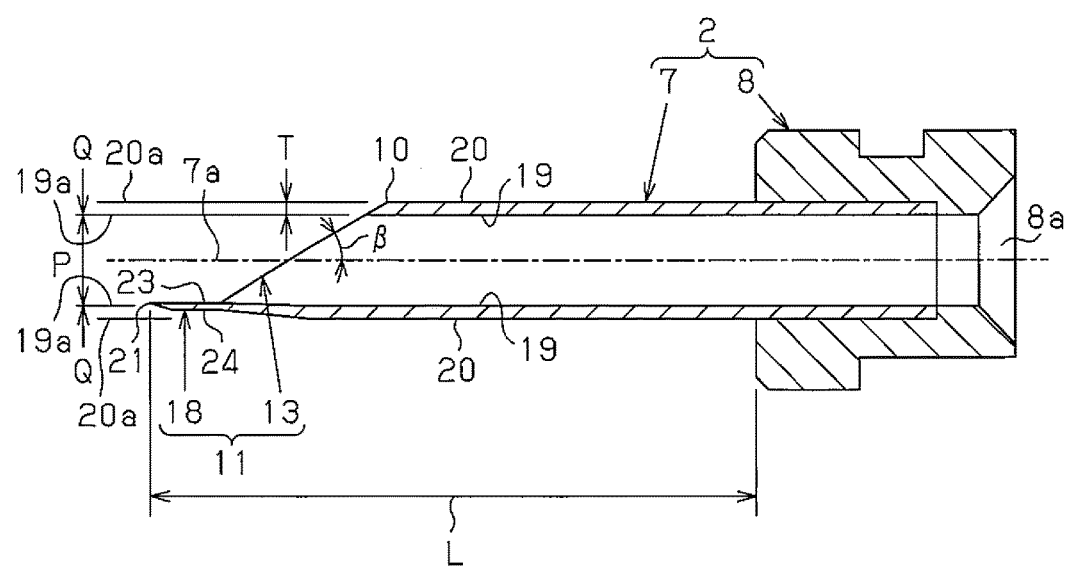
FIG. 2B is a cross-sectional view of the trocar of FIG. 2A.

As shown in FIGS. 1A to 1D, the holder 3 includes a grip handle 4, a coupling arm 5, and a guide rod 6. The grip handle 4 is molded from plastic. The coupling arm 5 projects from the distal end face of the grip handle 4. The guide rod 6 is formed of metal and is inserted and placed in the distal end face of the grip handle 4 next to the coupling arm 5. As shown in FIG. 1D, the insertion tube 2 includes a metal guide tube 7 and a collar 8 molded from plastic. The outer circumferential portion of the proximal end of the guide tube 7 is inserted in the collar 8. As shown in FIG. 2B, a tube inlet 8a extends through the inside of the collar 8. A tube outlet 10 is formed at the distal end of the guide tube 7 of the insertion tube 2 to communicate with the tube inlet 8a of the collar 8. As shown in FIGS. 1C and 1D, a flat anti-rotation surface 9 is formed on the outer circumference of the collar 8. As shown in FIGS. 1B and 1D, when the guide rod 6 is inserted in the tube inlet 8a of the collar 8, the coupling arm 5 of the grip handle 4 comes into surface contact with the anti-rotation surface 9 of the collar 8. The anti-rotation surface 9 prevents rotation of the insertion tube 2 about the axis of the guide rod 6 by the surface contact. In this manner, the insertion tube 2 is detachably engaged with the holder 3.

An incision blade 11 is integrally molded with the guide tube 7 at the tube outlet 10 of the guide tube 7. The incision blade 11 is molded through processes shown in FIGS. 4A to 4F.

In the process shown in FIG. 4A, a cylindrical tubular member 12 molded of stainless-steel or titanium is prepared. In the process shown in FIG. 4B, the distal end of the tubular member 12 is cut at an angle to form a cut portion 15. The cut portion 15 has a cutout area 13, which includes an inclined surface 13a. The inclined surface 13a inclines such that the distance from the center line 12a of the tubular member 12 decreases from the proximal end of the tubular member 12 toward the distal end of the tubular member 12. The inclined surface 13a is continuous with a distal end face 14 of the tubular member 12 to intersect the distal end face 14 at a predetermined angle.

In the process shown in FIG. 4C, the distal end face 14 of the cut portion 15 is pressed to form a flat plate-shaped first projecting portion 16. In the process shown in FIG. 4D, the first projecting portion 16 is further pressed to extend the first projecting portion 16 along the center line 12a of the tubular member 12 and form a flat rectangular plate-shaped second projecting portion 17, which is thinner and has a wider area than the first projecting portion 16. In the process shown in FIG. 4E, the second projecting portion 17 is trimmed to form a triangular blade plate portion 18a. In the process shown in FIG. 4F, outer blade edges 22 (see FIG. 2A) of the blade plate portion 18a on the outer circumferential surface of the guide tube 7 are sharpened. In this manner, a flat plate-shaped blade portion 18 is formed as shown in FIGS. 2A and 2B. The blade portion 18 extends from the tube outlet 10 of the guide tube 7, which is made by machining the tubular member 12, along the center line 7a of the guide tube 7 via the inclined surface 13a. Instead of the outer circumferential surface of the guide tube 7, the side of the blade plate portion 18a corresponding to the inner circumferential surface of the guide tube 7 may be sharpened, or the sides of the blade plate portion 18a corresponding to the outer circumferential surface and the inner circumferential surface of the guide tube 7 may be respectively sharpened.

As shown in FIG. 2B, the guide tube 7 has a thickness T between an inner circumferential surface 19 and an outer circumferential surface 20. The tube outlet 10 of the guide tube 7 is open on the inner side of the inclined surface 13a toward the blade portion 18.

Through the above-described processes, the incision blade 11 is integrally molded with the tube outlet 10 of the guide tube 7. The incision blade 11 includes the cutout area 13, which has the inclined surface 13a, and the blade portion 18, which is continuous with the cutout area 13.

As shown in FIGS. 2A, 2B and FIGS. 3A to 3D, the blade portion 18 has a distal blade edge 21, a pair of outer blade edges 22, an inner surface 23, and an outer surface 24.

Figure 3B:
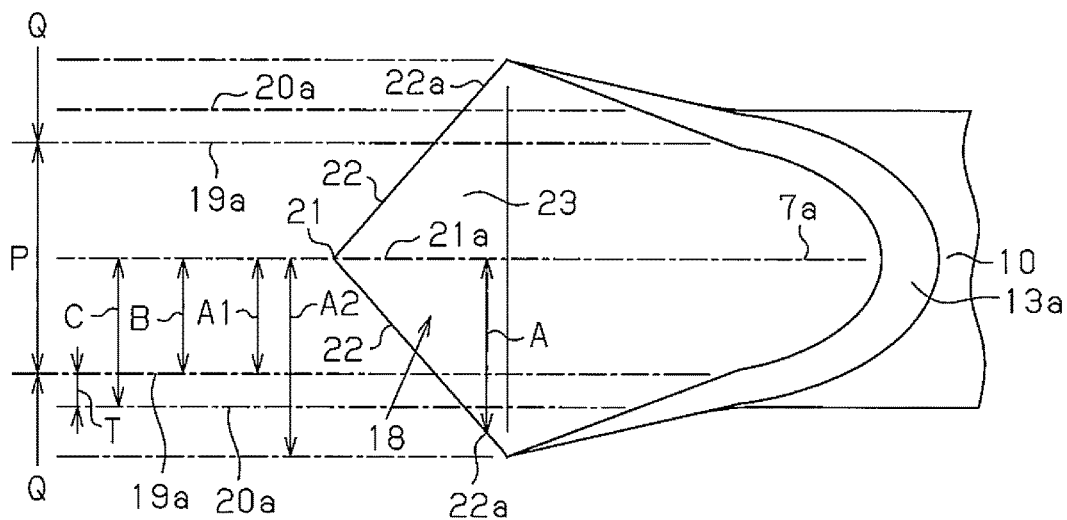
FIG. 3B is a partially enlarged plan view of the trocar according to the first embodiment.
Figure 3D:
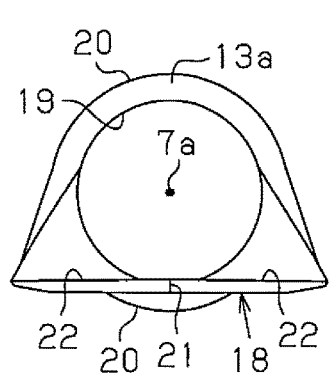
FIG. 3D is a partially enlarged side view of the trocar according to the first embodiment.
Figure 3A:
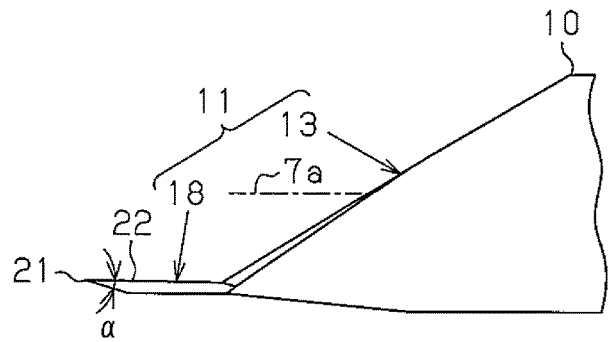
FIG. 3A is a partially enlarged front view of the trocar according to the first embodiment.
Figure 3C:
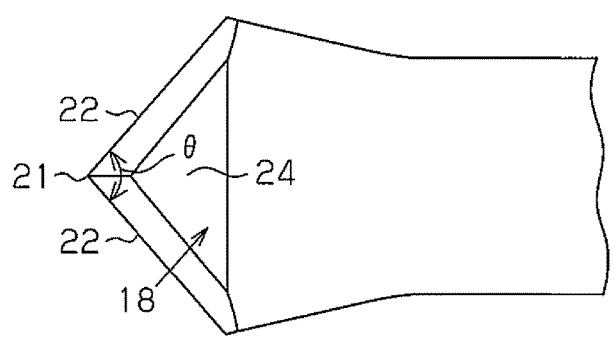
FIG. 3C is a partially enlarged bottom view of the trocar according to the first embodiment.

The distal blade edge 21 is located at the pointed distal end of the blade portion 18. As shown in FIG. 3C, the pair of outer blade edges 22 intersect at a predetermined crossing angle $\theta$ and extend continuously from the distal blade edge 21 toward the tube outlet 10. As shown in FIG. 3B, the outer blade edges 22 are symmetrical on both sides of a center line 21a of the guide tube 7 that passes through the distal blade edge 21 and extend such that the space between the outer blade edges 22 gradually increases from the distal blade edge 21 toward the tube outlet 10. The inner surface 23 is formed between the pair of outer blade edges 22 to be flat and continuous with the inner circumferential surface 19 of the tube outlet 10 and the inclined surface 13a. The outer surface 24 is formed between the pair of outer blade edges 22 to be flat and continuous with the outer circumferential surface 20 of the tube outlet 10.

The inclined surface 13a is formed to have a substantially U-shape such that the space in the width direction of the inclined surface 13a (direction orthogonal to the longitudinal direction of the insertion tube 2, which connects the tube inlet 8a of the collar 8 and the tube outlet 10) gradually increases toward the outer blade edges 22 of the blade portion 18. The outer blade edges 22 of the blade portion 18 are continuous with the inclined surface 13a.

As shown in FIG. 2B, the guide tube 7 is divided into an inner region P, which is on the inner side of a boundary surface 19a extending along the inner circumferential surface 19 of the tube outlet 10, and an outer region Q, which is on the outer side of the boundary surface 19a. The outer blade edges 22 of the blade portion 18 converge to the distal blade edge 21 to intersect each other within the range of the thickness T of the guide tube 7 between the boundary surface 19a, which extends along the inner circumferential surface 19, and a boundary surface 20a, which extends along the outer circumferential surface 20. The distal blade edge 21 of the blade portion 18 may slightly enter the inner region P in the vicinity of the boundary surface 19a. As shown in FIG. 2A, the outer blade edges 22 of the blade portion 18 separate in the width direction of the insertion tube 2. Each outer blade edge 22 includes an outermost blade edge 22a, which extends beyond the range of the thickness T of the guide tube 7 into the outer region Q. That is, each outer blade edge 22 of the blade portion 18 has the outermost blade edge 22a in the outer region Q. The distance A between each outermost blade edge 22a and the center line 7a of the insertion tube 2 is set to be greater than the inner radius B of the inner circumferential surface 19 of the guide tube 7 (A>B). The distance A between each outermost blade edge 22a and the center line 7a of the insertion tube 2 may also be set to be equal to the inner radius B of the inner circumferential surface 19 of the guide tube 7. The outermost blade edges 22a are the sections that determine the width of the incision.

As shown in FIG. 3B, the distance A between each outermost blade edge 22a and the center line 7a is set between a minimum distance A1 and a maximum distance A2. The minimum distance A1 is the distance between the center line 7a and the inner circumferential surface 19 of the guide tube 7. The maximum distance A2 is the distance between the center line 7a and the position where each end of the inclined surface 13a intersects the corresponding outer blade edge 22 in a direction orthogonal to the center line 7a. When the distance between the center line 7a of the insertion tube 2 and the outer circumferential surface 20 of the guide tube 7 is represented by C, the distance A can be set to be greater than or equal to the distance C and less than or equal to twice the distance C (C≤A≤2 C), and more particularly, the distance A is preferably set to be greater than or equal to the distance C and less than or equal to 1.5 times the distance C (C≤A≤1.5 C).

More specifically, the maximum distance A2 of the distance A related to the outermost blade edges 22a can be set to 0.1 to 1.8 mm, the inner radius B of the guide tube 7 can be set to 0.05 to 1.0 mm, the distance C of the guide tube 7, that is, the outer radius C can be set to 0.07 to 1.2 mm, and the thickness T (C−B) can be set to 0.02 to 0.8 mm. Furthermore, the crossing angle $\theta$ of the outer blade edges 22 can preferably be set to 30 to 120 degrees, and more preferably to 40 to 90 degrees. The sharpening angle α of the outer blade edges 22 can preferably be set to 10 to 60 degrees, and more preferably to 20 to 45 degrees. The inclination angle 13 of the inclined surface 13a with respect to the center line 7a of the insertion tube 2 can preferably be set to 10 to 60 degrees, and more preferably to 20 to 45 degrees. The distance L between the distal blade edge 21 and the collar 8 can preferably be set to 1 to 15 mm, and more preferably to 1 to 10 mm. The above-described parameters A, B, C, T, θ, α, β, L can be set to numerical values out of the above-described numerical value range.

The process for using the trocar 1 according to the first embodiment in vitreous surgery of the eyeball 25 will now be described.

The holder 3 is held and the trocar 1 is placed against the eyeball 25 shown in FIG. 8A. The incision blade 11 is then inserted into the eyeball 25 along the center line 7a of the insertion tube 2. This first causes the distal blade edge 21 of the incision blade 11 to start incising the eyeball 25, and subsequently the outer blade edges 22 of the incision blade 11 incise the eyeball 25 on both sides of the distal blade edge 21 in a straight line. Thus, a linear incision is made in the eyeball 25. The linear incision includes an incision made by the outermost blade edges 22a. Furthermore, when the trocar 1 is pushed into the vitreous body 25a in the eyeball 25 along the center line 7a of the insertion tube 2, the insertion tube 2 can be inserted and placed in the eyeball 25 through the incision with the incision blade 11 remaining in the eyeball 25. At this time, the incision is expanded, but the contraction force of the eyeball 25 presses the incision against the outer circumferential surface 20 of the insertion tube 2. The holder 3 is then detached from the insertion tube 2. In this manner, while one or two or more insertion tubes 2 are sequentially inserted and placed in the eyeball 25, a surgical instrument 26, such as a cutting tool, lighting device, or an infusion device for an artificial intraocular fluid, is inserted into the insertion tube 2 from the tube inlet 8a of the collar 8 and is made to project from the tube outlet 10. Thus, the surgical instrument 26 can be inserted into the vitreous body 25a in the eyeball 25 beside the incision blade 11. This reduces load applied to the incision when the surgical instrument 26 is used.

A second embodiment of the present invention will now be described with reference to FIGS. 5 to 7 and FIG. 8B focusing on differences from the first embodiment. FIGS. 5A, 5B, FIGS. 6A to 6D, FIGS. 7A to 7F, and FIG. 8B of the second embodiment correspond to FIGS. 2A, 2B, FIGS. 3A to 3D, FIGS. 4A to 4F, and FIG. 8A of the first embodiment.

Figure 5A:
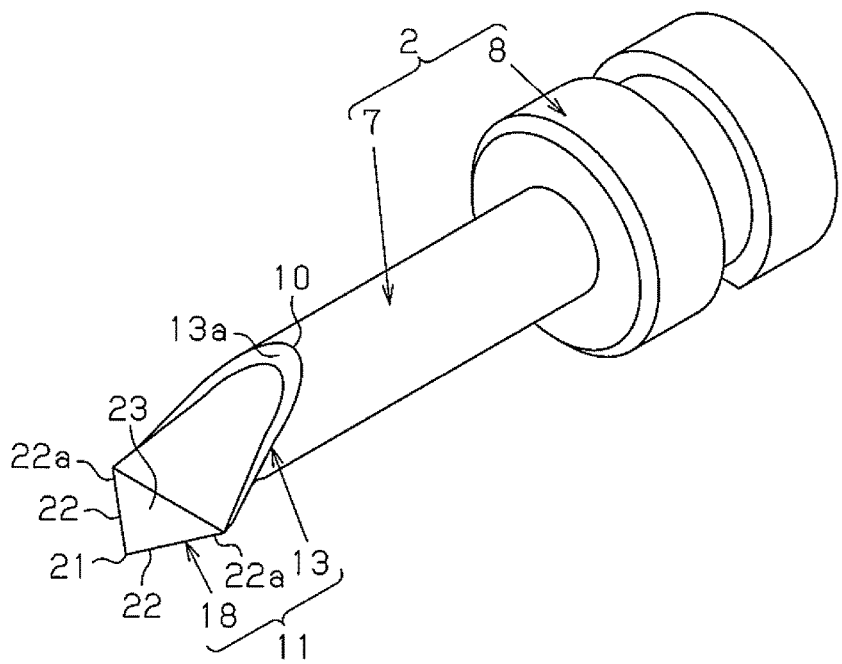
FIG. 5A is a perspective view of a trocar according to a second embodiment.
Figure 5B:
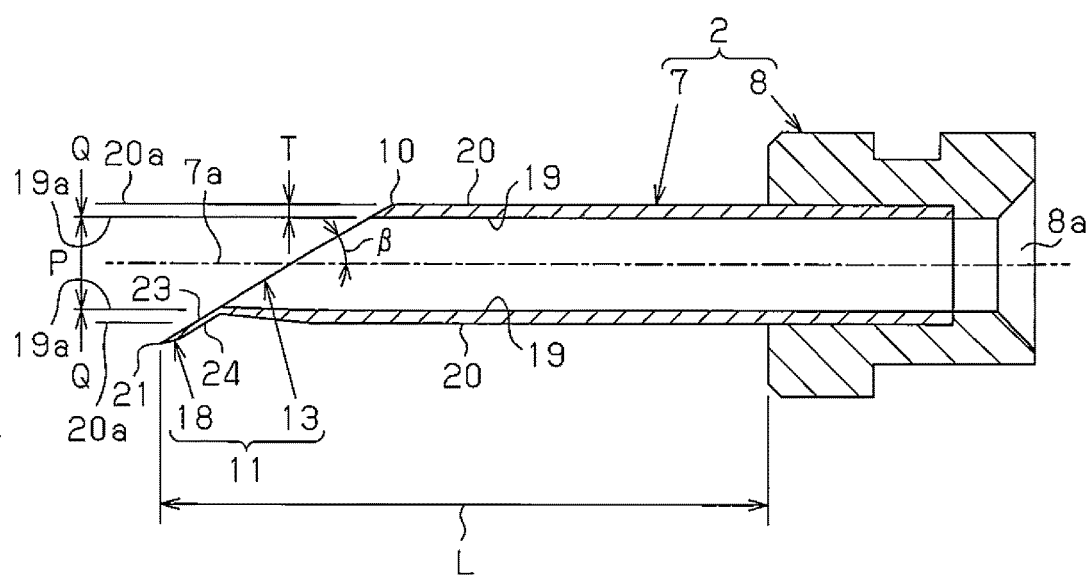
FIG. 5B is a cross-sectional view of the trocar of FIG. 5A.
Figure 6B:
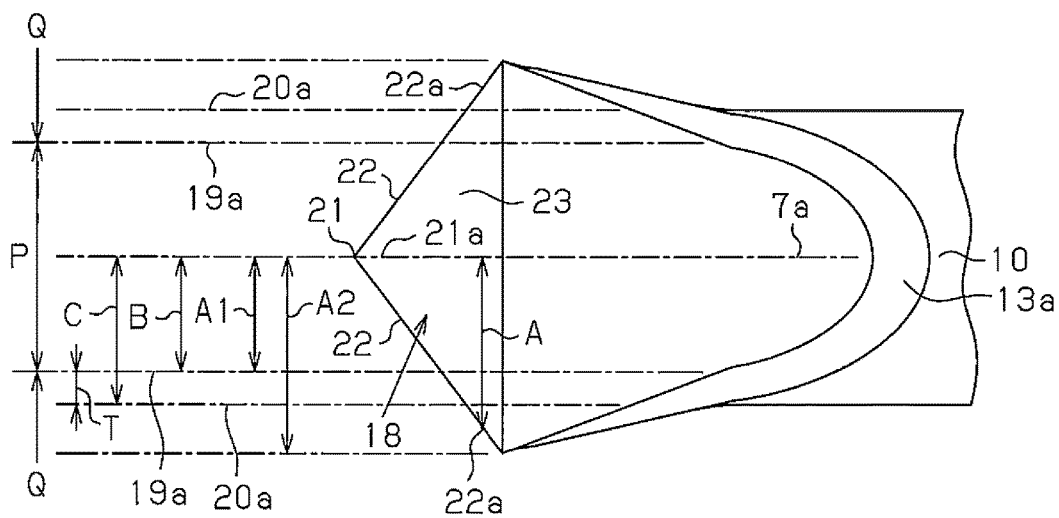
FIG. 6B is a partially enlarged plan view of the trocar according to the second embodiment.
Figure 6D:
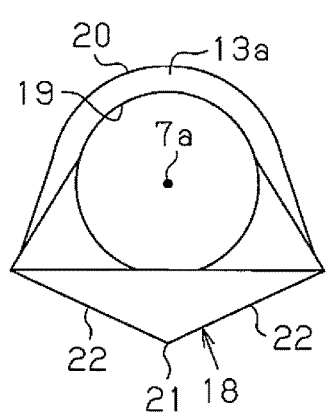
FIG. 6D is a partially enlarged side view of the trocar according to the second embodiment.
Figure 6A:
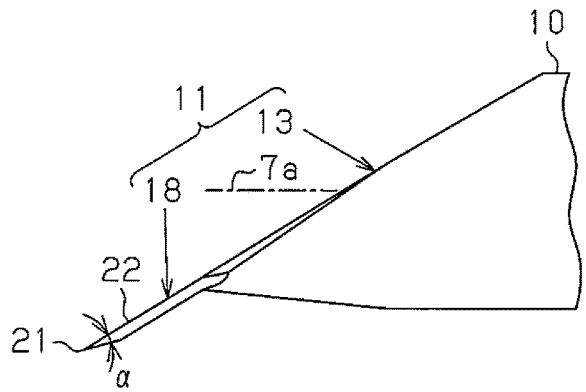
FIG. 6A is a partially enlarged front view of the trocar according to the second embodiment.
Figure 6C:
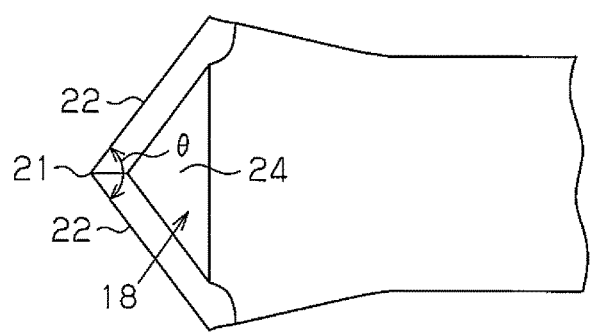
FIG. 6C is a partially enlarged bottom view of the trocar according to the second embodiment.

The trocar 1 of the second embodiment differs from the first embodiment in the form of the blade portion 18 of the incision blade 11. As shown in FIG. 5B, the blade portion 18 of the incision blade 11 extends from the cutout area 13 along the inclined surface 13a. As shown in FIG. 5B, when the insertion tube 2 is viewed from the side, the distal blade edge 21 of the blade portion 18 is located in the outer region Q beyond the range of the thickness T of the guide tube 7 between the boundary surface 19a, which extends along the inner circumferential surface 19, and the boundary surface 20a, which extends along the outer circumferential surface 20. As shown in FIG. 6B, when the insertion tube 2 is viewed from above, the outer blade edges 22 of the blade portion 18 are separate from each other in the width direction of the insertion tube 2. Each outer blade edge 22 has the outermost blade edge 22a, which extends into the range of the outer region Q beyond the range of the thickness T of the guide tube 7.

The distance A between each outermost blade edge 22a and the center line 7a of the insertion tube 2 is set to be greater than the outer radius C of the outer circumferential surface 20 (A>C>B). The distance A between each outermost blade edge 22a and the center line 7a of the insertion tube 2 may be set to be equal to the outer radius C of the outer circumferential surface 20 of the guide tube 7. The distance A related to the outermost blade edges 22a is set between the above-mentioned minimum distance A1 and the maximum distance A2. When the distance between the center line 7a of the insertion tube 2 and the outer circumferential surface 20 of the guide tube 7 is represented by C, the distance A can be set to be greater than or equal to the distance C and less than or equal to twice the distance C (C≤A≤2 C), and more particularly, the distance A is preferably set to be greater than or equal to the distance C and less than or equal to 1.5 times the distance C (C≤A≤1.5 C).

The incision blade 11 is integrally formed with the tube outlet 10 of the guide tube 7 through the processes shown in FIGS. 7A to 7F in the manner similar to the first embodiment. In the present embodiment, except the process shown in FIG. 7D, the processes shown in FIGS. 7A, 7B, 7C, 7E, 7F are the same as the processes of the first embodiment shown in FIGS. 4A, 4B, 4C, 4E, 4F. Thus, detailed explanations of the processes of FIGS. 7A, 7B, 7C, 7E, 7F are omitted.

In the process shown in FIG. 7D, the first projecting portion 16 is pressed to extend the first projecting portion 16 and form a flat plate-shaped second projecting portion 17, which is thinner than the first projecting portion 16. Then, the second projecting portion 17 is bent to extend along the inclined surface 13a of the tubular member 12.

Since the procedure for using the trocar 1 according to the second embodiment is also basically the same as that of the first embodiment, only the differences from the first embodiment will be discussed below.

In the second embodiment, since the blade portion 18 extends along the inclined surface 13a, the insertion tube 2 is tilted. In this state, the blade portion 18 is placed against the eyeball 25 in substantially the same manner as the first embodiment to make a linear incision. The insertion tube 2 is then returned to the state before being tilted and is inserted and placed in the eyeball 25 through the incision.

The first and second embodiments have the following advantages.

(1) In the first embodiment and the second embodiment, the incision blade 11 is provided at the tube outlet 10 of the insertion tube 2, and the tube outlet 10 is configured to open toward the incision blade 11. Thus, when the incision blade 11 is inserted in the eyeball 25 to make an incision, the insertion tube 2 can be inserted and placed in the eyeball 25 through the incision with the incision blade 11 remaining in the eyeball 25. Since insertion of the incision blade 11 and insertion and placing of the insertion tube 2 are continuously performed, operation for inserting and placing the trocar 1 is easy.

(2) In the first embodiment and the second embodiment, the surgical instrument 26 can be inserted in the insertion tube 2 from the collar 8 to project from the tube outlet 10 with the incision blade 11 remaining in the eyeball 25. Thus, the incision blade 11 does not need to be withdrawn from the insertion tube 2 after the insertion tube 2 is inserted and placed in the eyeball 25. This facilitates operation for inserting and placing the trocar 1.

Blade edges 22a of the incision blade 11 are located in the outer region Q of the insertion tube 2, the width dimension of the incision blade 11 is set to be greater than the outer diameter of the insertion tube 2. Thus, the incision dimension of the incision will be greater than the outer diameter of the insertion tube 2. Therefore, when the insertion tube 2 is inserted and placed in the eyeball 25 through the incision, load is unlikely to be applied to the incision, allowing the incision to heal easily.

(4) In the first embodiment and the second embodiment, the distance A between each outermost blade edge 22a of the incision blade 11 and the center line 7a of the insertion tube 2 is set to be greater than the inner radius B between the center line 7a and the inner circumferential surface 19 of the tube outlet 10. Thus, the width dimension of the incision blade 11 can be set to be greater than the inner radius of the insertion tube 2. Therefore, the incision dimension of the incision will also be increased, and when the insertion tube 2 is inserted and placed in the eyeball 25 through the incision, load is unlikely to be applied to the incision by the insertion tube 2, allowing the incision to heal easily.

(5) In the first embodiment and the second embodiment, the distance A between the center line 7a of the insertion tube 2 and each outermost blade edge 22a of the incision blade 11 in the width direction of the insertion tube 2 is set to be greater than the outer radius C between the center line 7a and the outer circumferential surface 20 of the tube outlet 10. Thus, the width dimension of the incision blade 11 can be set to be greater than the outer diameter of the insertion tube 2, and the incision dimension of the incision is further increased. When the insertion tube 2 is inserted and placed in the eyeball 25 through the incision, the incision is further prevented from being damaged by the insertion tube 2, allowing the incision to heal easily. Furthermore, since the distance A is set to be less than twice the outer radius C, the incision is prevented from becoming larger than necessary, reducing load on a patient.

(6) In the first embodiment, the blade portion 18 of the incision blade 11 extends along the center line 7a of the insertion tube 2. In the second embodiment, however, the blade portion 18 of the incision blade 11 extends along the inclined surface 13a of the incision blade 11. Thus, in the second embodiment, although the incision blade 11 is kept at the tube outlet 10 of the insertion tube 2, the blade portion 18 does not come in the way when the surgical instrument 26 is inserted in the insertion tube 2 since the blade portion 18 having the distal blade edge 21 and the outer blade edges 22 is further separated from the inner circumferential surface 19 of the insertion tube 2.

(7) In the second embodiment, the blade portion 18 of the incision blade 11 extends along the inclined surface 13a of the incision blade 11. In the first embodiment, however, the blade portion 18 of the incision blade 11 extends along the center line 7a of the insertion tube 2. Thus, in the first embodiment, the blade portion 18 is easily inserted in the eyeball 25.

(8) In the first embodiment and the second embodiment, in order to manufacture the trocar 1, the distal end of the tubular member 12 is cut to provide the cutout area 13, which is cut in a direction inclined with respect to the center line 12a of the tubular member 12. Subsequently, the cut portion 15 is pressed to form the projecting portion 16, 17, which is then trimmed to form the blade plate portion 18a. The blade plate portion 18a is then sharpened to form the blade portion 18. In this manner, the incision blade 11 is easily formed integrally at the end of the tubular member 12.

The above described embodiments may be modified as follows.

In the first embodiment and the second embodiment, the shape of the incision blade 11 is set such that a linear incision is made in the eyeball 25. Although not shown, the shape of the incision blade 11 may be changed such that an arcuate incision is made in the eyeball 25. Furthermore, the shape of the incision blade 11 may be changed such that multiple linear incisions or multiple arcuate incisions are made at the outer circumference of the inner region P to be arranged side by side in the circumferential direction of the insertion tube 2.

Although not shown, the outer blade edges 22 of the blade portion 18 may be straight, curved, or a combination of straight and curved forms.

Although not shown, when the surgical instrument 26 having a relatively small outer diameter compared with the inner radius of the guide tube 7 is used, the surgical instrument 26 can be smoothly inserted and removed through the guide tube 7. In this case, the distal blade edge 21 of the blade portion 18 may be located in the inner region P, and part of the outer blade edges 22 of the blade portion 18 extending from the distal blade edge 21 may be located in the inner region P.

Although not shown, in the incision blade 11, the distal blade edge 21 of the blade portion 18 does not need to be a sharp point, but may be a sharp linear edge.

Although not shown, as for the blade portion 18 of the incision blade 11, instead of a blade having the pair of outer blade edges 22, a blade having multiple outer blade edges 22 arranged at equal circumferential angles around the center line 7a of the insertion tube 2 or a blade having a single outer blade edge 22 may be employed.

Although not shown, the incision blade 11 may be formed separately instead of being formed integrally with the tube outlet 10 of the insertion tube 2. In this case, the incision blade 11 is configured to be attachable to the tube outlet 10.

Although not shown, the guide tube 7 of the insertion tube 2 does not need to be formed into an annular shape that is continuous in the circumferential direction like in the first embodiment, but may be formed into an annular shape having a partially cut-out portion in the circumferential direction.

Although not shown, the guide tube 7 of the insertion tube 2 may be changed to have a shape other than a circular cross-section.

Although not shown, the guide rod 6 may be omitted from the holder 3. Instead, the holder 3 may include multiple arms to sandwich the outer surface of the collar 8 so that the holder 3 holds the collar 8 using the arms.

Although not shown, the collar 8 may be omitted from the insertion tube 2.

In the insertion tube 2, the material of the guide tube 7 may be changed to material other than metal such as plastic.

In each of the above-described embodiments, the tubular member 12, which is used as the material for the guide tube 7, is cylindrical. Instead of the cylindrical material, a flat plate may be used as the material for the guide tube 7. A portion corresponding to the cutout area 13 or the blade portion 18 may be formed in advance in the plate material, which is then rolled to form a tube. The guide tube 7 may be formed in this manner.

Although not shown, the tubular member 12 having the shape shown in the process of FIG. 4E or FIG. 7E may be formed by injection molding using metal powder or plastic. In this case, the processes of FIGS. 4A to 4D or FIGS. 7A to 7D may be omitted.

Although not shown, the inner circumferential surface 19 and the outer circumferential surface 20 of the insertion tube 2 or the inner surface 23 and the outer surface 24 of the blade portion 18 may be subjected to a coating process or a surface modification process using fluoropolymer or silicone rubber. This reduces frictional resistance of the insertion tube 2 or the blade portion 18 with respect to, for example, the rim of the incision.

Although not shown, a valve for preventing leakage of intraocular fluid from the inside of the eyeball 25 may be provided in the collar 8 or in the vicinity of the collar 8. In this case, the valve may be provided in a state in which the collar 8 is separate from the holder 3, or the collar 8 may be coupled to the holder 3 with the valve being provided.

Although not shown, the trocar may be used for an affected area in a laparoscopic surgery instead of the eyeball. In this case, the above-described various parameters (such as the distance A, B, C, L, the angle θ, α, β) may be changed in accordance with the affected area.

DESCRIPTION OF THE REFERENCE NUMERALS

1 . . . trocar, 2 . . . insertion tube, 7a . . . center line of insertion tube, 8a . . . tube inlet, 10 . . . tube outlet, 11 . . . incision blade, 12 . . . tubular member, 12a . . . center line of tubular member, 13 . . . cutout area, 13a . . . inclined surface, 14 . . . end face of tubular member, 15 . . . cut portion, 16, 17 . . . projecting portion, 18a . . . blade plate portion, 18 . . . blade portion, 19 . . . inner circumferential surface of tube outlet, 19a . . . boundary surface, 20 . . . outer circumferential surface of tube outlet, 21 . . . distal blade edge, 22 . . . outer blade edges, 22a . . . outermost blade edges, P . . . inner region, Q . . . outer region.

What is claimed:

1. A trocar comprising an insertion tube, wherein the insertion tube includes:
    a tube inlet located at a proximal end of the insertion tube; and
    a tube outlet that communicates with the tube inlet and is located at a distal end of the insertion tube,
    the insertion tube includes an incision blade at the distal end,
    the tube outlet opens toward the incision blade, and an end face of the tube outlet has an inclined surface that is inclined with respect to a center line of the insertion tube, and
    the incision blade includes:
        a distal blade edge, which is located at a pointed distal end of the incision blade and is configured to start to incise an affected area when the distal blade edge is inserted in the affected area; and
        a pair of outer blade edges that each extend from the distal blade edge toward the tube outlet of the insertion tube, the distal blade edge of the incision blade is located at a position where the outer blade edges of the incision blade intersect each other,
    the insertion tube is divided into an inner region, which is inside a boundary surface along an inner circumferential surface of the tube outlet, and an outer region, which is outside the boundary surface, and
    a blade portion, which includes the distal blade edge and the outer blade edges, is flat plate-shaped,
    the outer blade edges are each sharpened at a predetermined angle, symmetrical on both sides of the center line that passes through the distal blade edge, and continuous with the inclined surface,
    the outer blade edge includes an outermost blade edge located in the outer region,
    wherein the distal blade edge of the incision blade is located in the outer region, and
    wherein a crossing angle of the outer blade edges in set to be 40 and 90 degrees.

2. A trocar comprising an insertion tube according to claim 1, wherein
    the distance between the center line of the insertion tube and the outermost blade edge is set to be greater than the distance between the center line of the insertion tube and the inner circumferential surface of the tube outlet.

3. The trocar according to claim 2, wherein, in a width direction orthogonal to the center line of the insertion tube, the distance between the center line of the insertion tube and the outermost blade edge is set to be greater than the distance between the center line of the insertion tube and an outer circumferential surface of the tube outlet.

4. The trocar according to claim 1, wherein
    the incision blade is configured to be inserted in the affected area to form an incision in the affected area, and the insertion tube is configured to be allowed to be inserted and placed in the affected area through the incision with the incision blade remaining in the affected area.

5. The trocar according claim 1, wherein the outer blade edge of the incision blade is one of a plurality of outer blade edges located on an outer circumference of the center line of the insertion tube.

6. The trocar according to claim 1, wherein the inclined surface is formed such that a space inside the inclined surface in the width direction of the insertion tube orthogonal to a longitudinal direction of the insertion tube gradually increases toward the outer blade edge of the incision blade.

7. The trocar according to claim 1, wherein the incision blade is formed integrally with the tube outlet.

8. The trocar according to claim 1, wherein a holder is detachably coupled to the tube inlet of the insertion tube.

9. The trocar according to claim 1, wherein a sharpening angle of the outer blade edges is set to be 20 to 45 degrees.

10. A method for manufacturing the trocar of claim 1, comprising:
    forming a cutout area by cutting an end of a tubular member such that the cutout area is inclined with respect to a center line of the tubular member, and forming a cut portion by leaving part of an end face of the tubular member to be continuous with the cutout area;
    forming a flat projecting portion by pressing the cut portion;
    forming a blade plate portion by trimming the flat projecting portion; and
    forming a blade portion by sharpening the blade plate portion.

* * * * *